United States Patent [19]
Gravenstein et al.

[11] Patent Number: 5,643,202
[45] Date of Patent: Jul. 1, 1997

[54] NASOPHARYNGEAL WASH COLLECTION DEVICE

[75] Inventors: Stefan Gravenstein, Madison; Peter Alan Shult, Stoughton; Barbara Ann Miller, Madison, all of Wis.; James Norman Lowder, Pleasanton, Calif.

[73] Assignees: Specollector, Inc., Stoughton, Wis.; Becton Dickinson and Company, Franklin Lakes, N.J.

[21] Appl. No.: 527,970

[22] Filed: Sep. 14, 1995

[51] Int. Cl.$^6$ .................................................. A61M 31/00
[52] U.S. Cl. .......................................................... 604/54
[58] Field of Search .................. 128/200.14, 200.21, 128/200.22, 200.23; 604/49, 54, 94, 93, 131, 257, 27

[56] References Cited

U.S. PATENT DOCUMENTS

| | | | |
|---|---|---|---|
| 2,577,321 | 12/1951 | Filger | 128/200.22 |
| 2,672,141 | 3/1954 | Filger | 128/200.22 |
| 5,116,311 | 5/1992 | Löfstedt | 128/200.22 |

FOREIGN PATENT DOCUMENTS

| | | | |
|---|---|---|---|
| 513751 | 6/1955 | Canada | 128/200.22 |
| 6707659 | 12/1967 | Netherlands | 128/200.22 |

*Primary Examiner*—Vincent Millin
*Assistant Examiner*—Manuel Mendez
*Attorney, Agent, or Firm*—Dewitt Ross & Stevens

[57] ABSTRACT

A self-contained device for rapid and repetitive delivery and collection of a fluid. The device includes a container having resilient walls and a lower portion in which the walls converge to form an inverted, generally elliptical frustum that pools the fluid stored in the container. The device also includes a nozzle having a funnel-shaped opening which facilitates discharge and collection of the fluid.

20 Claims, 7 Drawing Sheets

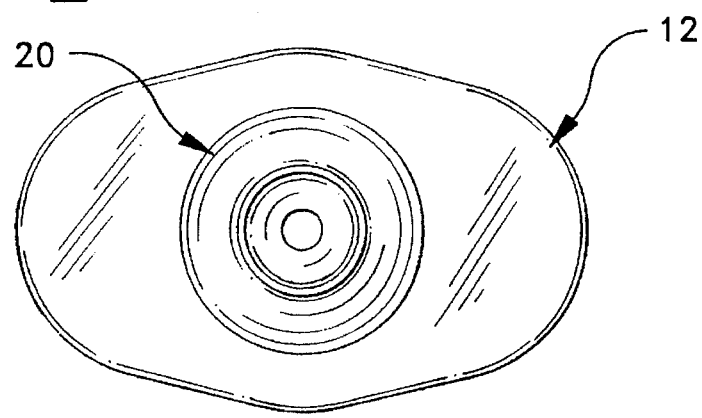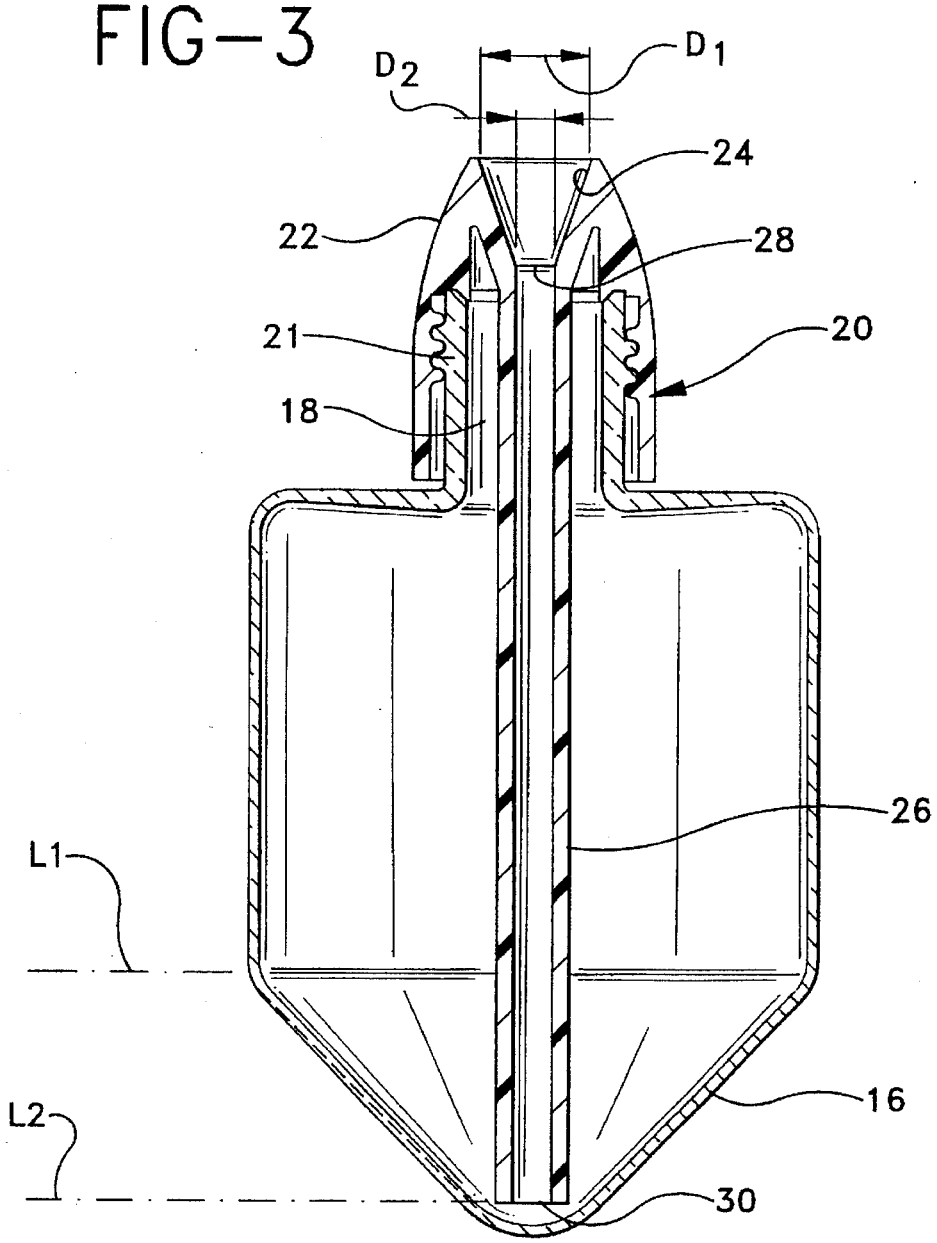

NASOPHARYNGEAL WASH COLLECTION DEVICE

BACKGROUND OF THE INVENTION

The present invention relates to a device for delivering and collecting fluids and, more particularly, to a self-contained manual device adapted for rapid and repetitive delivery and collection of a fluid.

Oftentimes, as part of a medical procedure, a physician is required to collect a specimen for culture (typically a fluid secretion) from a body cavity of a patient. The medical procedure may, for example, require that a specimen be taken from the patient's nasopharynx.

Typically, these specimens are obtained by direct swabbing of the affected area. However, a more accurate and preferred method for collecting a specimen involves the delivery of a quantity of irrigating solution to the nasopharynx (thereby dissolving the secretion in the solution) and the subsequent collection of such solution for analysis in a laboratory.

The goal of the above-described collection technique is to obtain a specimen having a high concentration of fluid secretion. This task is preferably accomplished by repeatedly lavaging the nasopharynx with the irrigating solution. Accordingly, it is important that the lavaging step be conducted with only a minimal loss of irrigating solution. Further, the process is preferably accomplished by employing only a relatively small volume of irrigating solution. In this fashion, the collected secretion does not become overly diluted in the irrigating solution and hinder the analysis stage. Finally, the process is preferably accomplished without causing undue discomfort or trauma to the patient.

The devices and techniques currently available are unable to simultaneously accomplish these goals. For example, at least one of the devices currently available for sampling the nasopharynx requires substantial wall suction that may prove uncomfortable and traumatic to the patient. Other devices such as bulb syringes are unable to effectively deliver fluid against gravity and, further, are not adapted for aspiration of the dispensed fluid. Moreover, typical sampling techniques require substantial cooperation from and movement by the patient, thereby rendering such techniques useless in children and the elderly.

One technique currently employed by physicians involves the construction of a collection device from a syringe, which is then filled with saline and fitted with a section of flexible catheter. The patient is placed in a generally horizontal position and, thereafter, the flexible catheter is advanced into the nasal cavity. The solution is then dispersed into the nasal cavity from the syringe and, thereafter, is aspirated back into the syringe. As might be expected, it is difficult to recollect the solution in the syringe because the solution tends to run back along the nasal passage. Further, the flexible catheter employed to deliver the solution does not facilitate the recovery process and, in fact, hinders the process due to the rather small diameter of its opening. Finally, the above-described procedure can be quite discomforting to the patient and is difficult to perform on children and the elderly.

It is also necessary, at times, to obtain specimens from such body cavities as the ear, vagina or rectum. For example, vaginal or rectal sampling is often required to check for local infections. These samples, which are currently obtained by swabbing the affected area or by sampling excrement, would prove more accurate and be accomplished in a less invasive manner by use of the above-described collection technique.

There is also a need in the medical field for a device which can deliver medication to a body cavity. The device is preferably capable of delivering a relatively large volume of medication to a body cavity. The particular procedure may also require that the delivered medication be promptly removed from the body cavity of the patient. For example, when treating a cancer of the nasal passage, it may prove medically desirable to deliver a relatively large volume, high concentration of a toxic agent to the passage. This agent must be quickly and entirely delivered to the nasal cavity and then quickly and entirely withdrawn. Again, the devices currently available are unable to accomplish this task.

There is a further need in the art for a device which would allow cleansing of a surface through repetitive lavaging of such surface with an irrigating solution. Accordingly, this same device must be capable of readily collecting the discharged solution once such solution has pooled.

SUMMARY OF THE INVENTION

The present invention, which addresses the needs of the prior art, provides a self-contained manual device for delivering and collecting fluid. The device includes a container for holding the fluid. This container includes an opening along its upper portion for transfer of the fluid to and from the container. The container also includes means for pooling the fluid. The pooling means is distally spaced from the opening. The device of the present invention also includes a nozzle removably securable to the opening. The nozzle is configured to facilitate discharge and collection of the fluid. The device further includes means for pressurizing and depressurizing the interior volume of the container. Finally, the device of the present invention includes fluid communication means extending between the nozzle and the pooling means and providing a flow path for the fluid whereby pressurization of the interior volume results in discharge of the fluid from the container and depressurization of the interior volume results in aspiration of the flow into the container.

In a preferred embodiment of the present invention, the pooling means is an inverted generally elliptical-shaped frustum formed in the lower portion of the container. Preferably, this frustum is substantially symmetric about an axis passing through the tube whereby the pooled fluid has its greatest depth along the axis when the device is maintained in a substantially verticle orientation. This preferred embodiment also includes resilient walls exhibiting elastic memory which allow an individual to squeeze the container thereby discharging the fluid. Finally, in this preferred embodiment of the present, invention, the nozzle includes a funnel-shaped port for facilitating discharge and collection of the fluid and, further, is shaped for sealing engagement of a body cavity.

The present invention also provides a method for obtaining a specimen from a body cavity. The method includes the step of providing a container for holding fluid. This container includes an opening along its upper portion for transfer of the fluid to and from the container. The container also includes means for pooling the fluid. The pooling means is distally spaced from the opening. The container also includes a nozzle removably securable to the opening and configured to facilitate discharge and collection of the fluid. The container further includes fluid communication means connected on one end to the nozzle and on the other to the pooling means for providing a flow path for the fluid. The method also includes the step of filling the container with a sufficient quantity of the fluid. The method includes the further step of pooling the fluid in the lower portion of the container such that the other end of the fluid communication means is submersed in fluid thereby forming a fluid seal. The method includes the additional step of maintaining the fluid seal surrounding the other end of the communication means. The method also includes the step of occluding the entrance of the body cavity with the nozzle. The method includes the further step of pressurizing the interior volume of the container whereby the fluid is forced from the pooling means into the other end of the fluid communication means, through the fluid communication means and out of the nozzle. Finally, the method includes the step of depressurizing the interior volume of the container whereby a negative pressure is created in the container tending to aspirate the fluid into the container.

The present invention also provides a method for effectively treating an internal surface of a body cavity with a medicine. The method includes the step of providing a container for holding fluid. This container includes an opening along its upper portion for transfer of the fluid to and from the container. The container also includes means for pooling the fluid. The pooling means is distally spaced from the opening. The container also includes a nozzle removably securable to the opening and configured to facilitate discharge and collection of the fluid. The container further includes fluid communication means connected on one end to the nozzle and on the other to the pooling means for providing a flow path for the fluid. The method also includes the step of filling the container with a desirable amount of medicine. The method includes the additional step of pooling the medicine in the lower portion of the container such that the other end of the fluid communication means is submersed in fluid thereby forming a fluid seal. Further, the method includes the step of maintaining the fluid seal surrounding the other end of the fluid communication means. The method includes the additional step of occluding the entrance of the body cavity with the nozzle. The method includes the further step of pressurizing the interior volume of the container whereby a predetermined volume of the medicine is forced from the pooling means into the other end of the communication means, through the fluid communication means and out of the nozzle. Finally, the method includes the step of depressuring the interior volume of the container whereby a negative pressure is created in the container attending to aspirate substantially all of the medicine into the container.

As a result, the present invention provides a self-contained manual device which enables rapid, simple, non-threatening and atraumatic sampling of body cavities such as the nasopharynx, ear, vagina or rectum. Particularly, fluid is introduced and recovered from a non-closed space by the alternate application of positive and negative pressure. The device permits repetitive lavaging of affected surfaces, allowing maximum sample recovery in a small volume of irrigant. Further, the shape of the nozzle permits comfortable occlusion of the entrance of the body cavity, particularly the external naris.

The present invention also provides a device suitable for obtaining specimens for culture from such body orifices as the vagina or rectum and provides a method for collecting such samples in a more accurate and less invasive manner.

The present invention also provides a device capable of rapidly delivering a relatively large volume of medicine to a body cavity. This same device is also capable of rapidly and entirely withdrawing the delivered medicine. Moreover, the device of the present invention allows cleansing of a surface through repetitive lavaging and is adapted to readily collect pooled solutions.

BRIEF DESCRIPTION OF THE DRAWINGS

FIG. 2 is a top plan view of the device of the present invention;

FIG. 3 is a front elevational view, in section, of the device of the present invention;

DETAILED DESCRIPTION OF THE INVENTION

Figure 1:
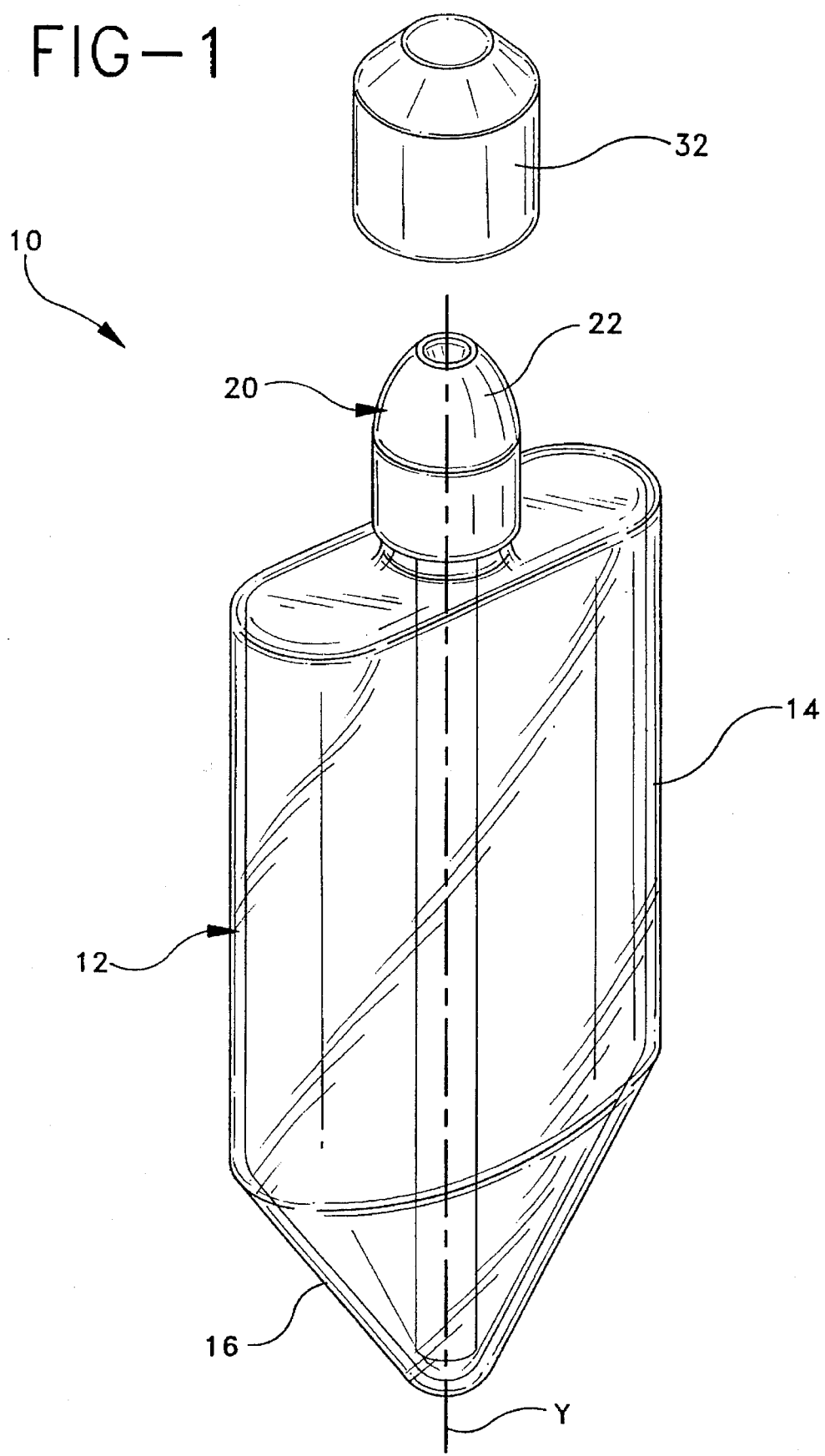
FIG. 1 is a perspective view of the self-contained manual fluid delivery and collection device of the present invention.

Referring to the drawings, a device 10 for delivering and collecting fluids is shown in FIG. 1. Device 10 includes a generally, elliptical-shaped container 12 having resilient walls 14. The walls of the container begin to converge in the lower portion of the container, resulting in a bottom 16 having the general configuration of an inverted, generally elliptical frustum. This frustum is symmetrical about an axis Y that passes through the container. Container 12 also includes an opening 18 (shown in FIG. 3) formed in its upper portion and a nozzle 20 removably secured thereto. Nozzle 20 is preferably secured to a neck 21 of container 12.

Nozzle 20 preferably includes a dome-shaped lip 22 configured to occlude the entrance to a body cavity and which facilitates sealing of the nozzle with such entrance during use. As best shown in FIG. 3, nozzle 20 is formed with a port 24 that converges in diameter from $D_1$ at the apex of lip 22 to $D_2$ at the junction of the port and a discharge tube 26. Port 24 both facilitates discharge of solution from the container (i.e., by diffusing the discharged solution) and also facilitates collection of the solution from the body cavity (i.e., by providing a large diameter opening to guide the returning solution back into the container).

As shown in FIG. 3, discharge tube 26 has a first end 28 which is connected to nozzle 20, and a second end 30 which extends into and terminates in the lowermost region of the frustum. The internal diameter of the tube, which establishes the flow path of the solution, communicates with the innermost portion of the port. As shown, the tube is preferably formed integral with the nozzle so that the nozzle and tube may be removed as one unit. Of course, the tube may also be fabricated separate from the nozzle. Other embodiments, for example, an embodiment in which a plurality of tubes are employed or an embodiment in which the tube(s) is formed integral with the walls, are also contemplated.

When the container is filled to level $L_1$ with fluid, all of the fluid is held in the frustum of the container while such container is maintained in a generally verticle orientation (as depicted in FIG. 3). It is readily apparent from the figures that the depth of the fluid (as measured in the frustum) will be greatest along axis Y. This is true even as the total level of fluid in the container is depleted because the converging walls of bottom 16 tend to pool the fluid at the central (or deepest) portion of the frustum. Other design structures, in which the fluid is also pooled at the first end of the discharge tube, are also contemplated.

Accordingly, it is possible, through the design of the present invention, to discharge substantially all of the solution in the container (i.e., until the solution reaches L2), while simultaneously maintaining a fluid seal at end 30 of discharge tube 26. It is desirable to maintain this fluid seal to maximize the pressure differential created by alternately squeezing and releasing the walls of the container. Particularly, the positive pressure created by squeezing the walls of the container propels the solution out the container, while the negative pressure created when the walls are released draws the solution back into the container.

As described, device 10 is preferably fabricated from a resilient material (e.g., plastic or rubber) that allows compression of the container. This compression of the container forces fluid from the frustum of the container into end 30 of the discharge tube, through the discharge tube, and out through port 24 of the nozzle. Preferably, the material employed to fabricate the container exhibits elastic memory such that the container will return to its original configuration once the compression force is removed therefrom. In a preferred embodiment of the present invention, the container is fabricated from a transparent material which allows viewing of the solution contained therein.

Figure 8:
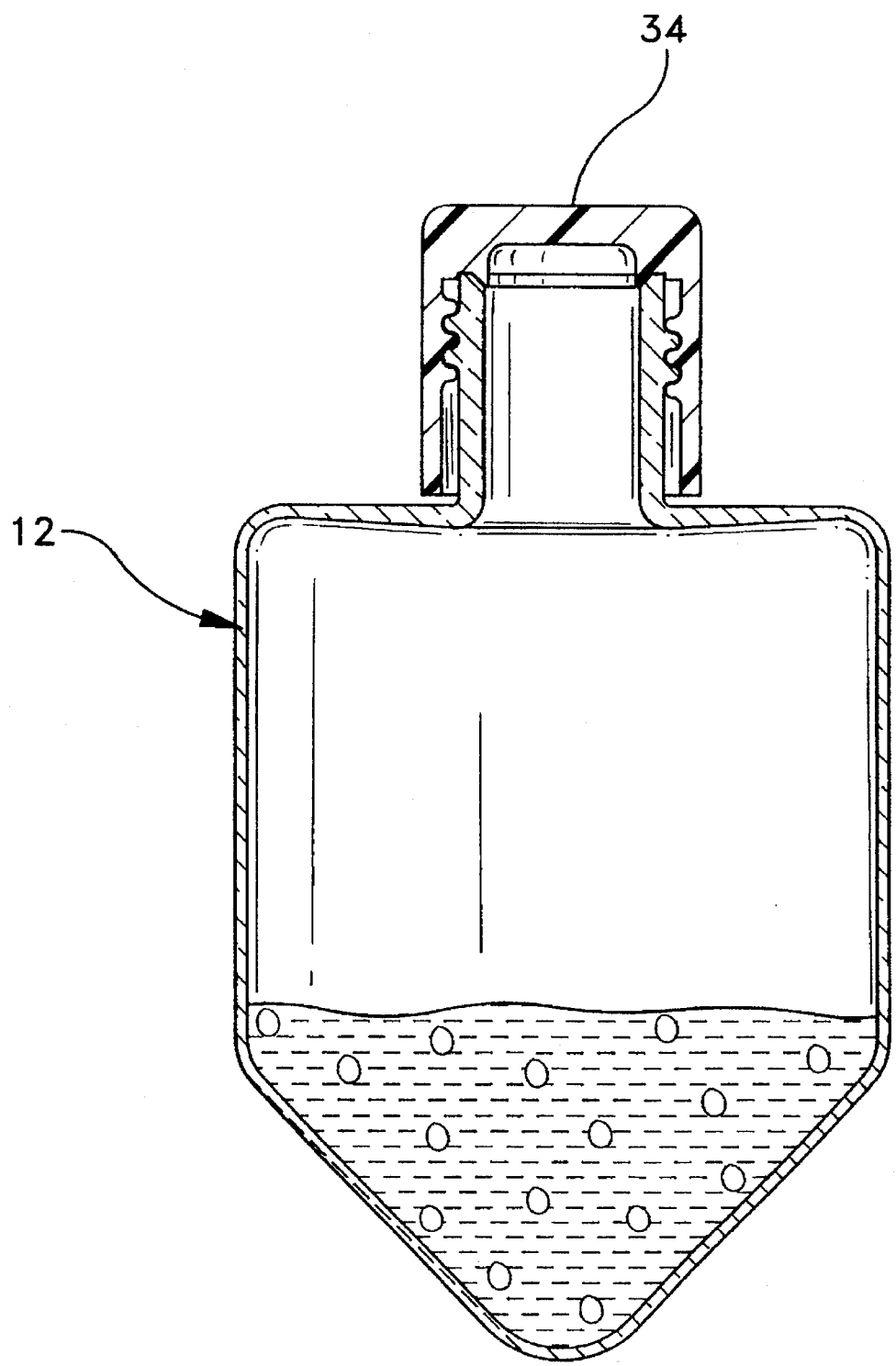
FIG. 8 shows the device of the present invention with its nozzle and discharge tube removed and with a closure cap engaged on the neck of the container.

Device 10 may include a cover 32 (shown in FIG. 1) for placement over nozzle 20 when the device is not in use. Device 10 may also include a closure cap 34 (shown in FIG. 8) for sealing the container following the sampling procedure and removal of the nozzle and tube unit.

Figure 4:
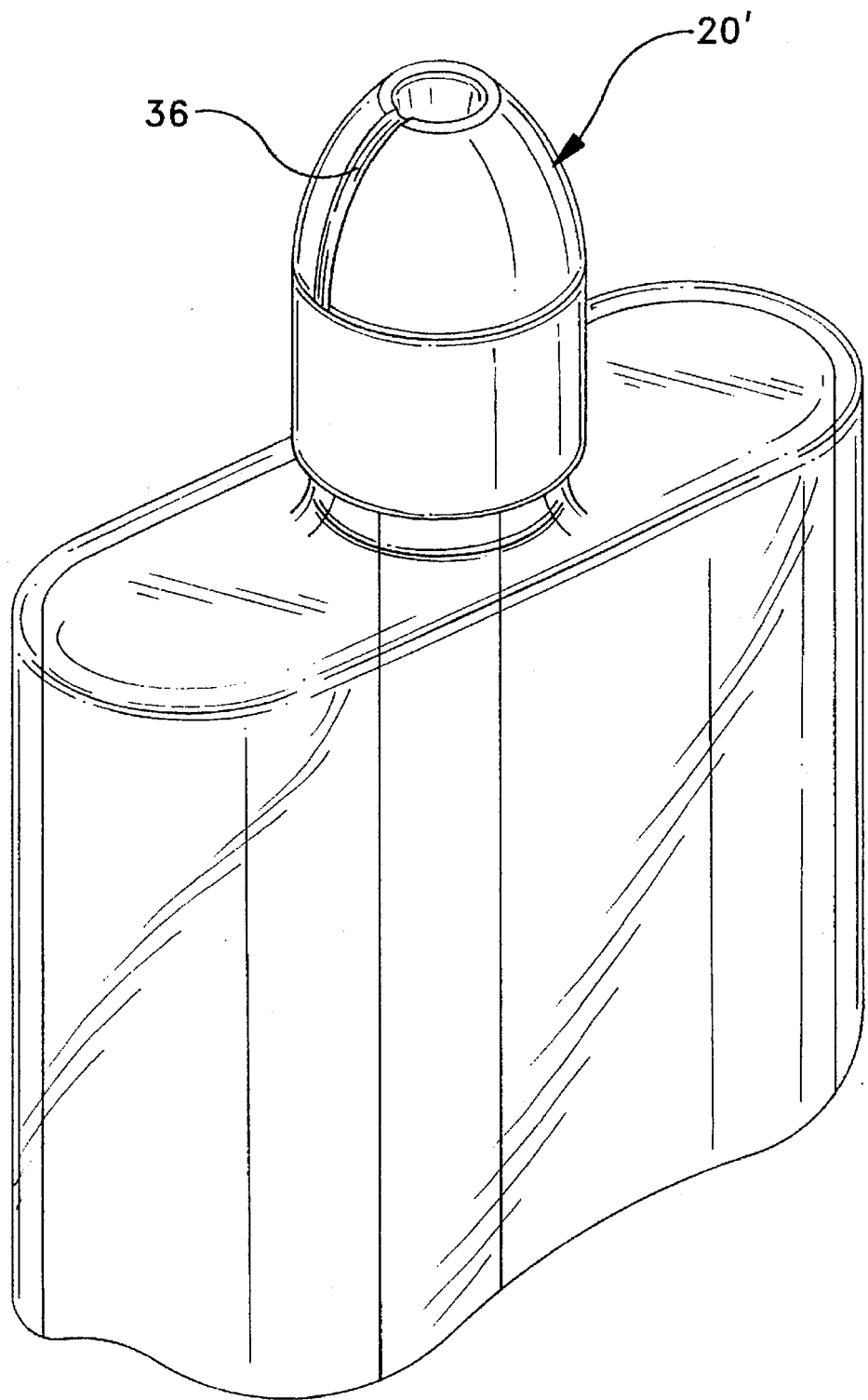
FIG. 4 is a perspective view of an alternative embodiment which includes a pressure relief groove formed in the nozzle.

In an alternative embodiment of the present invention, the nozzle, i.e., nozzle 20' shown in FIG. 4, is formed with a pressure relief groove 36. Relief groove 36 is formed in nozzle 20' to allow use of the present invention in applications wherein the creation of large pressure differentials is undesirable, such as collecting a specimen from the ear canal or delivering medication to the ear canal. Particularly, the inclusion of the relief groove allows the device to function in substantially the same fashion, but without creating pressure differentials of the same degree in the patient's body cavity.

Figure 5:
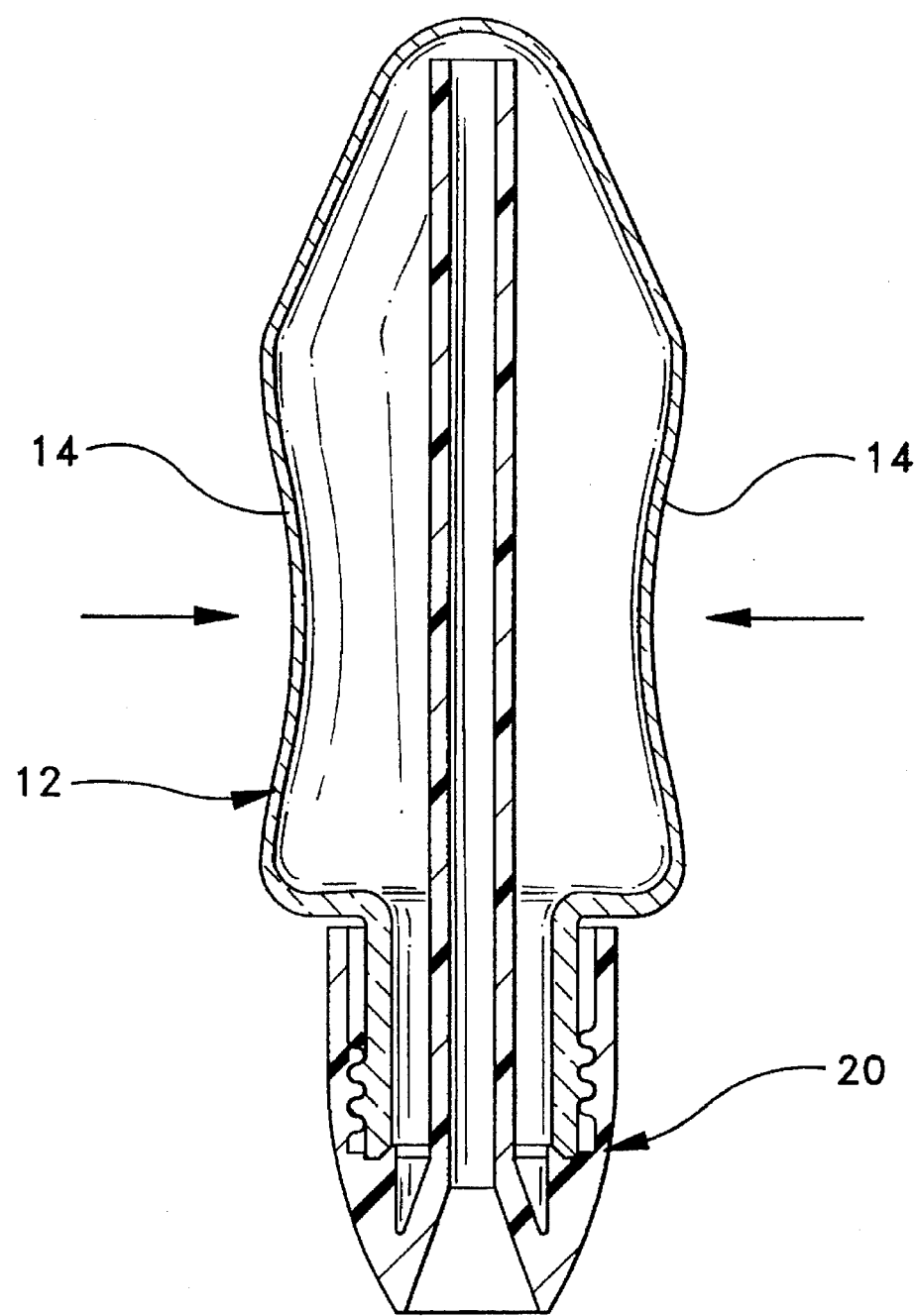
FIG. 5 is a side elevational view, in section, of the device of the present invention in an inverted state and with the resilient walls of such device squeezed inward due to a compression force.
Figure 6:
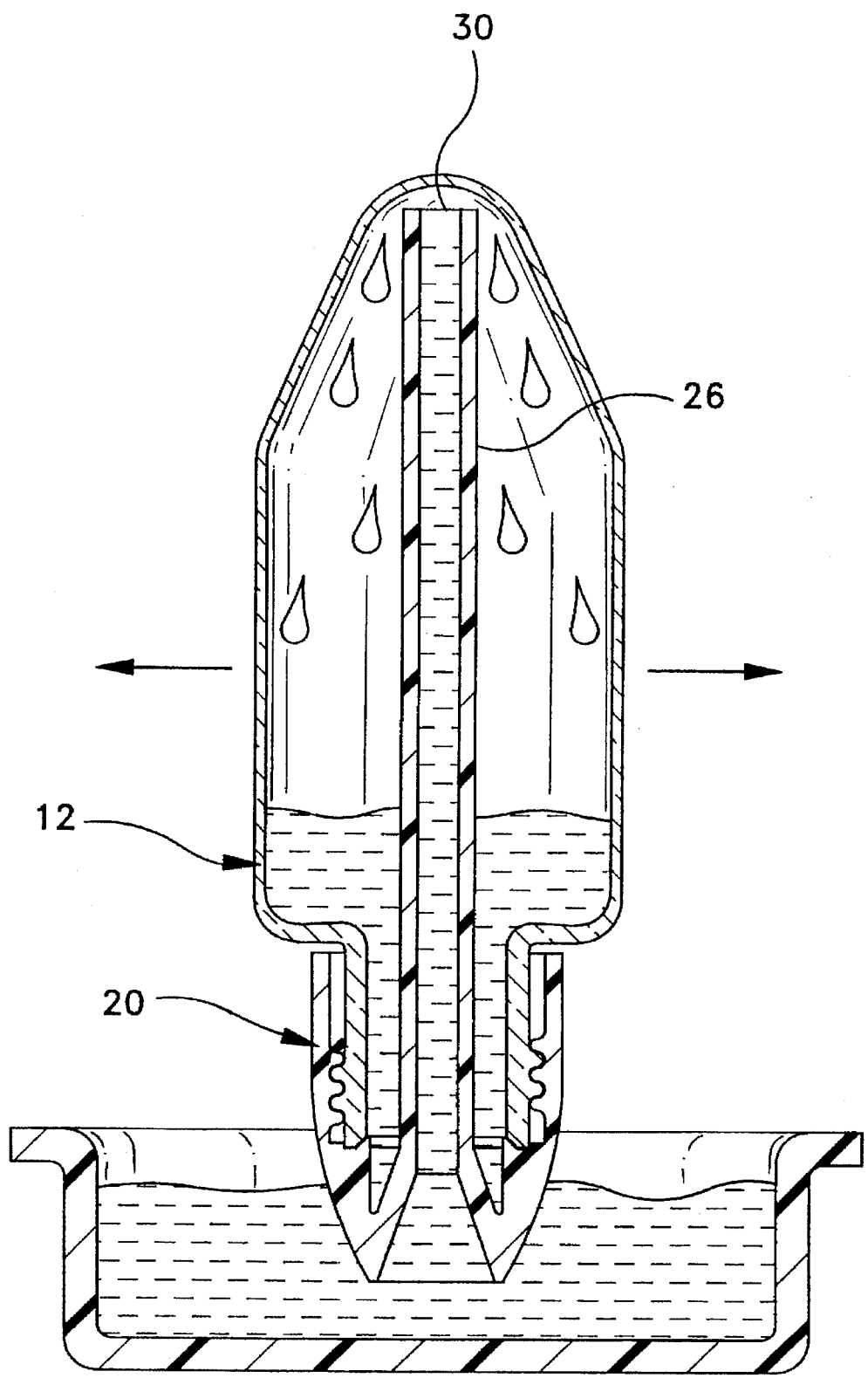
FIG. 6 is a side elevational view, in section, showing the device of the present invention being filled with a fluid.

The use of the present invention will now be explained with reference to FIGS. 5 to 8 and with reference to a sampling of the nasopharynx of a patient. As shown in FIG. 5, the container is initially empty prior to use. Cover 32 is removed and container 12 is inverted. The resilient walls of the container are then compressed, thereby forcing a volume of air out of the container.

At this point, the nozzle is submersed in a solution (see FIG. 6) and the compression force is released from the container. Once the compression force is released, the walls (due to the inherent memory of the plastic) return to their initial configuration, thereby creating a negative pressure in the container which draws the solution into the container.

Figure 7:
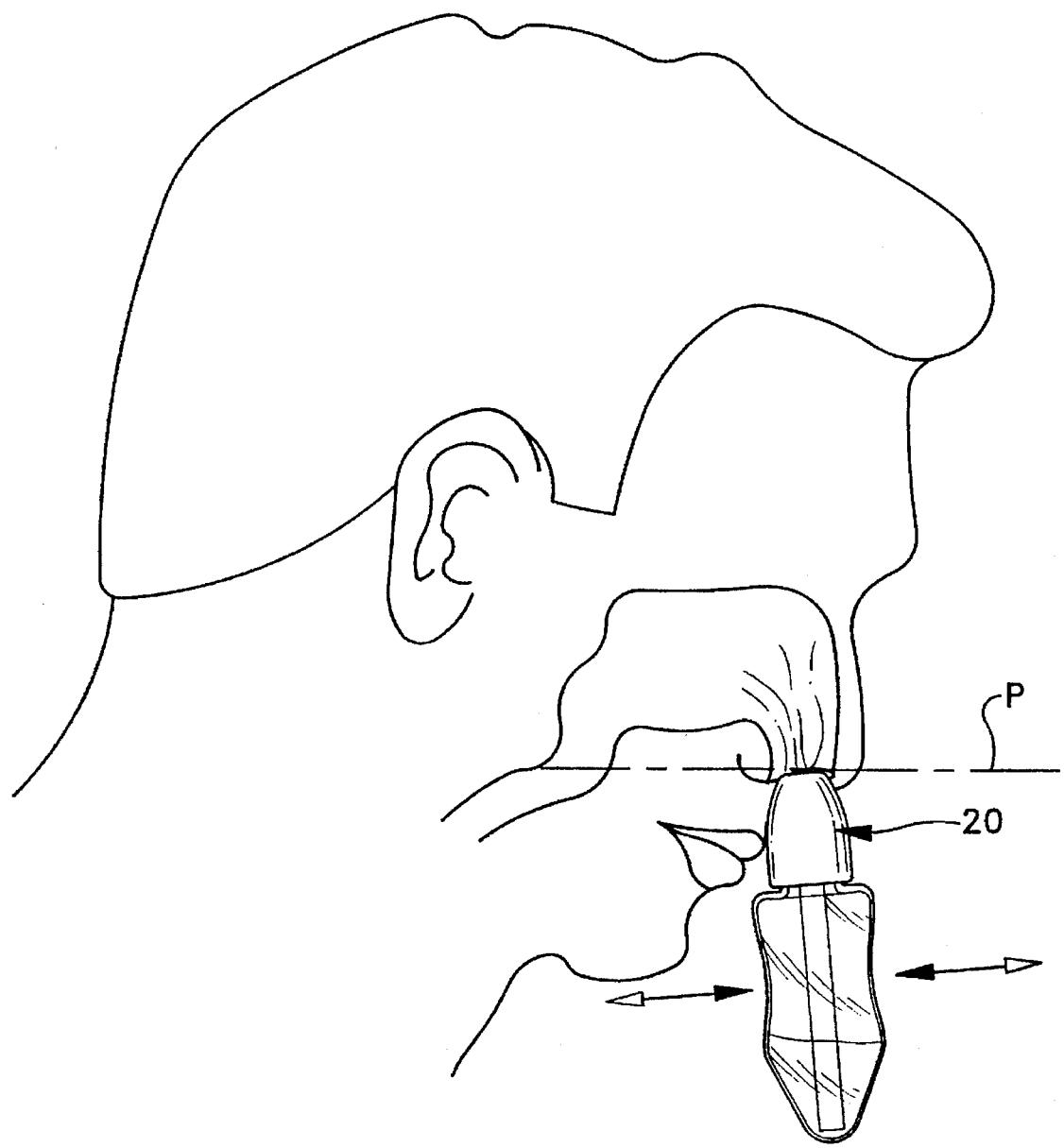
FIG. 7 shows the device of the present invention discharging fluid into the nasopharynx of an individual.

Next, as shown in FIG. 7, the patient's head is tilted slightly forward until the entrance to the nostril is substantially parallel to a level plane P. The device, which is maintained in a substantially vertical orientation, is then positioned under the nostril. The nozzle of the device is inserted into the nostril until a seal is formed between the nozzle and the nostril. The other nostril of the patient is pinched closed.

The resilient walls of the container are then squeezed to deliver the solution. Specifically, by squeezing the resilient walls of the container, a positive pressure is created in the container which forces the fluid from the frustum, into the discharge tube, and out of the nozzle. The container is squeezed until the level of solution in the container drops to L2. At this point, substantially all of the solution has been delivered to the nasopharynx. Further, because the fluid seal has been maintained at end 30 of the discharge tube and because the seal between the nostril and nozzle has been maintained, a negative pressure will be created when the walls of the container are released.

Accordingly, after an appropriate period of time, the physician releases the walls of the container to allow the walls to return to their initial configuration. As the walls expand outward, a negative pressure is developed in the bottle. The combination of gravity and negative pressure substantially draws the entire volume of dispensed solution back into the container. The design of port 24 also facilitates this collection process.

Once the solution is collected in the container, the discharge and collection process can be repeated. After the sampling procedure is completed, the nozzle and attached transfer tube may be removed and discarded, securing cap 34 placed over the opening (see FIG. 8), and the container and entire contents forwarded to an appropriate facility for analysis.

The same procedure is employed to sample other body cavities such as the ear, vagina or rectum. As mentioned, the use of device 10 to collect samples from such cavities provides more accurate specimens and accomplishes the sampling procedure in a less invasive manner than the prior art devices and techniques. A similar discharge and collection procedure may also be employed to cleanse an internal body surface. As is apparent from the above-description, the fluid seal is eliminated When device 10 is inverted. Once inverted, the device can be readily employed to aspirate pooled solutions.

Further, the above-described procedure is particularly well-suited for delivery of medicine to a body cavity (e.g., the nasopharynx, ear, eye, vagina, rectum). As mentioned, certain medical procedures require the application and prompt removal of medicine to and from a body cavity (e.g., the treatment of a cancer of the nasal passage). The present invention allows a physician to consistently accomplish this task. Similarly, the present invention allows a physician to accurately deliver a known quantity of medicine to a body cavity, particularly in those medical procedures which require that a predetermined amount of medicine be applied to the body surface.

Thus, while there have been described what are presently believed to be the preferred embodiments of the invention, those skilled in the art will realize that various changes and modifications may be made to the invention without departing from the spirit of the invention, and it is intended to claim all such changes and modifications which fall within the scope of the invention.

What is claimed is:

1. A self-contained manual device for delivering and collecting fluid, comprising:
  a container for holding said fluid, said container including
    an opening for transfer of said fluid to and from said container, said opening being surrounded by a neck, said container also including means for pooling said fluid, said pooling means distally spaced from said opening;
  a nozzle removably securable to said neck, said nozzle configured to facilitate discharge and collection of said fluid;
  means for pressurizing and depressurizing the interior volume of said container; and
  fluid communication means extending between said nozzle and said pooling means for providing a flow path for said fluid whereby pressurization of said interior volume results in discharge of said fluid from said container and depressurization of said interior volume results in aspiration of said fluid into said container;

in combination with a cap sized to removably engage said neck when said nozzle is removed.

2. The device according to claim 1, wherein said pooling means comprises an inverted generally elliptical-shaped frustum formed on the entirety of said lower portion of said container.

3. The device according to claim 2, wherein said fluid communication means comprises a tube having first and second ends, and wherein said first end of said tube communicates with said nozzle and said second end of said tube communicates with said pooling means.

4. The device according to claim 3, wherein said frustum is substantially symmetric about an axis passing through said tube whereby the pooled fluid has its greatest depth along said axis when said device is maintained in a substantially verticle orientation.

5. The device according to claim 1, wherein both said neck and said nozzle are threaded to allow engagement therebetween.

6. The device according to claim 1, wherein said nozzle includes a funnel-shaped port for facilitating discharge and collection of said fluid.

7. The device according to claim 1, wherein said nozzle is shaped for sealing engagement with the entrance of a body cavity.

8. The device according to claim 7, wherein said nozzle is dome-shaped to occlude said entrance during use.

9. The device according to claim 8, wherein said nozzle is configured to occlude the external naris.

10. The device according to claim 1, wherein said container includes resilient walls exhibiting elastic memory which allow an individual to squeeze said container thereby discharging said fluid.

11. The device according to claim 1, wherein said nozzle includes a pressure relief groove extending downwardly from the opening and along the outer surface of the nozzle for reducing the pressure differential created through use of said device.

12. The device according to claim 1, further comprising a cap sized to cover said nozzle when said container is not in use.

13. A method for obtaining a specimen from a body cavity, comprising:

providing a container for holding fluid, said container including an opening for transfer of said fluid to and from said container, said container also including means for pooling said fluid, said pooling means distally spaced from said opening, said container also including a nozzle removably securable to said opening and configured to facilitate discharge and collection of said fluid, said container further including fluid communication means connected on one end to said nozzle and on the other to said pooling means for providing a flow path for said fluid;

filling said container with a sufficient quantity of said fluid;

pooling said fluid in said lower portion of said container such that said other end of said fluid communication means is submersed in fluid thereby forming a fluid seal;

maintaining the fluid seal surrounding said other end of said communication means;

occluding the entrance of said body cavity with said nozzle;

pressurizing the interior volume of said container whereby said fluid is forced from said pooling means into said other end of said fluid communication means, through said fluid communication means and out of said nozzle;

depressurizing the interior volume of said container whereby a negative pressure is created in said container tending to aspirate said fluid into said container.

14. The method according to claim 13, wherein the step of pressurizing the interior volume of said container comprises the application of radial force to the walls of said container; and wherein the step of depressurizing the interior volume of such container comprises the release of said radial force from said container.

15. The method according to claim 13, further comprising the step of maintaining said container in a substantially vertical orientation.

16. The method according to claim 13, wherein said fluid communication means comprises a discharge tube, and wherein said discharge tube and said nozzle form an integral unit, and further comprising the steps of removing said integral unit and sealing said container with a cap.

17. The method according to claim 13, further comprising the step of analyzing the fluid aspirated into said container.

18. A method for effectively treating an internal surface of a body cavity with a medicine, comprising:

providing a container for holding fluid, said container including an opening for transfer of said fluid to and from said container, said container also including means for pooling said fluid, said pooling means distally spaced from said opening, said container also including a nozzle removably securable to said opening and configured to facilitate discharge and collection of said fluid, said container further including fluid communication means connected on one end to said nozzle and on the other to said pooling means for providing a flow path for said fluid;

filling said container with a desirable amount of medicine;

pooling said medicine in said lower portion of said container such that said other end of said fluid communication means is submersed in fluid thereby forming a fluid seal;

maintaining the fluid seal surrounding said other end of said fluid communication means;

occluding the entrance of said body cavity with said nozzle;

pressurizing the interior volume of said container whereby a predetermined volume of said medicine is forced from said pooling means into said other end of said communication means, through said fluid communication means and out of said nozzle;

depressurizing the interior volume of said container whereby a negative pressure is created in said container tending to aspirate substantially all of said medicine into said container.

19. The method according to claim 18, wherein the step of pressurizing the interior volume of said container comprises the application of radial force to the walls of said container; and wherein the step of depressurizing the interior volume of said container comprises the release of said radial force from said container.

20. The method according to claim 18, further comprising the step of analyzing the fluid aspirated into said container.

* * * * *